US005952288A

United States Patent [19]

Durbut et al.

[11] Patent Number: 5,952,288

[45] Date of Patent: Sep. 14, 1999

[54] PROTEIN CONTAINING CLEANING COMPOSITIONS

[75] Inventors: Patrick Durbut, Verviers; Guy Broze, Grace-Hollogne, both of Belgium

[73] Assignee: Colgate-Palmolive Co., Piscataway, N.J.

[21] Appl. No.: 08/944,341

[22] Filed: Oct. 6, 1997

[51] Int. Cl.$^{6}$ .............................. C11D 17/00; A61K 7/30

[52] U.S. Cl. .......................... 510/426; 510/127; 510/365; 510/428

[58] Field of Search .................................... 510/424, 426, 510/428, 405, 127, 119, 365

[56] References Cited

U.S. PATENT DOCUMENTS

| | | | |
|---|---|---|---|
| 4,076,800 | 2/1978 | Marsh et al. | 424/70 |
| 4,087,518 | 5/1978 | Smith et al. | 424/70 |
| 4,115,548 | 9/1978 | Marsh et al. | 424/70 |
| 4,705,682 | 11/1987 | Moeller et al. | 424/70 |
| 5,665,693 | 9/1997 | Kroner et al. | 510/476 |
| 5,733,860 | 3/1998 | Durbut et al. | 510/405 |
| 5,854,194 | 12/1998 | Davister et al. | 510/422 |

*Primary Examiner*—Necholus Ogden
*Attorney, Agent, or Firm*—Richard E. Nanfeldt

[57] ABSTRACT

A composition comprising: a protein chemical linker, an anionic surfactant and water.

1 Claim, No Drawings

PROTEIN CONTAINING CLEANING COMPOSITIONS

FIELD OF THE INVENTION

The present invention relates to protein chemical linkers that can be added to a cleaning composition to improve particulate soil removal from the surface to which it has been applied.

BACKGROUND OF THE INVENTION

A major problem with microemulsion cleaning compositions such is that while these compositions exhibit excellent grease removal or a grease release effect that the removal is in need of improvement.

The instant invention solves this deficiency of particulate soil removal while providing compositions that still have excellent grease removal properties.

SUMMARY OF THE INVENTION

The present invention relates to chemical compositions which comprise approximately by weight of: a first anionic surfactant, optionally, a second surfactant selected from the group consisting of amine oxides, zwitterionics and alkylene carbonate surfactants, an animal or vegetable protein which is complexed with the anionic surfactant and water.

The instant compositions excluded the use of ethoxylated nonionic surfactants formed for the condensation product of primary or secondary alkanols and ethylene oxide or propylene oxides because the use of these ethoxylated nonionic would cause a weakening of the chemical association between the protein chemical linker and the anionic surfactant.

The complex of the anionic surfactant and protein chemical linker can be applied neat to the surface which is being treated, wherein the protein chemical linker functions to bind the surfactant to the treated surface.

DETAILED DESCRIPTION OF THE INVENTION

The present invention relates to a composition which comprises:

(a) 0.1 to 2 wt. %, more preferably 0.1 to 1.0 wt. % of an animal and/or vegetable protein;

(b) 0.5 to 30 wt. % of at least one anionic surfactant having a carboxylate, sulfate or sulfonate group;

(c) 0 to 15 wt. % of a second surfactant selected from the group consisting of an amine oxide surfactant, a zwitterionic surfactant and an alkylene carbonate surfactant and mixtures thereof, wherein the anionic surfactant complexes with the amine oxide, zwitterionic surfactant or alkylene carbonate, wherein the second surfactant complexes with the anionic surfactant to form an analephotropic negatively charged anionic complex;

(d) 0 to 10 wt. % of a perfume, essential oil or water insoluble hydrocarbon;

(e) 0 to 20 wt. % of a cosurfactant; and (f) 50 to 99.8 wt. % of water.

The compositions of the instant invention can be in the form of a solution, a microemulsion, a gel or a paste. The complex of the anionic surfactant and protein chemical linker can be made by simple mixing in water with or without heat.

The analephotropic negatively charged anionic complex which may be contained in the instant cleaning compositions such as a fabric cleaning composition, a light duty liquid composition, an all purpose or microemulsion composition, a body cleaning composition or a shampoo comprises a complex of:

(a) at least one anionic surfactant which is an alkali metal salt or an alkaline earth metal salt of a sulfonate or sulfate surfactant; and (b) an amine oxide, zwitterionic surfactant or alkylene carbonate surfactant wherein the ratio of the anionic surfactant to the amine oxide surfactant, zwitterionic surfactant or alkylene carbonate surfactant is 7:1 to 0.2:1, more preferably 2:1 to 0.4:1. The instant composition contains about 3 to about 40 wt. %, more preferably about 5 to about 20 wt. % of the analephotropic negatively charged complex.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and the salt-forming cation usually is selected from the group consisting of sodium, potassium, or magnesium, with the sodium and magnesium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3-(or higher) phenyl isomers and a correspondingly low content (well below 50%) of 2-(or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms and having the formula $RCH{=}CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an a-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos. 2,503,280; 2,507,088; 3,260,744; 3,372,188; and German Patent 735,096.

Examples of satisfactory anionic sulfate surfactants are the $C_8$–$C_{18}$ alkyl sulfate salts and the ethoxylated $C_8$–$C_{18}$ alkyl sulfate salts and the ethoxylated $C_8$–$C_{18}$ alkyl ether sulfate salts having the formula $R(OC_2H_4)_n$ $OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the ethoxylated alkyl ether sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. The ethoxylated alkyl ether sulfates differ from one another in the number of moles of ethylene oxide reacted with one mole of alkanol. Preferred alkyl sulfates and preferred ethoxylated alkyl ether sulfates contain 10 to 16 carbon atoms in the alkyl group.

The ethoxylated $C_8$–$C_{12}$ alkylphenyl ether sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)_nOX$ COOH wherein n is a number from 4 to 12, preferably 5 to 10 and X is selected from the group consisting of $CH_2$, $(C(O)R_1$ and

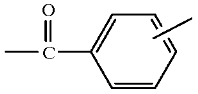

wherein $R_1$ is a $C_1$–$C_3$ alkylene group. Preferred compounds include $C_9$–$C_{11}$ alkyl ether polyethenoxy (7–9) C(O) $CH_2CH_2COOH$, $C_{13}$–$C_{15}$ alkyl ether polyethenoxy (7–9)

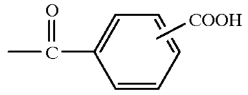

and $C_{10}$–$C_{12}$ alkyl ether polyethenoxy (5–7) $CH_2COOH$. These compounds may be prepared by considering ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

Of the foregoing non-soap anionic surfactants used in forming the analephotropic complex, the preferred surfactants are the sodium or magnesium salts of the $C_8$–$C_{15}$ alkyl mononuclear aromatic sulfonates such as magnesium linear $C_8$–$C_{15}$ alkyl benzene sulfonate and sodium linear $C_8$–$C_{15}$ alkyl benzene sulfonate and mixtures thereof.

Generally, the proportion of the nonsoap-anionic surfactant will be in the range of 0.5 to 30%, preferably from 1% to 15%, by weight of the cleaning composition.

The instant composition contains as part of the analephotropic negatively charged complex about 3% to about 15%, preferably about 4% to about 12% of an amine oxide, alkylene carbonate or zwitterionic surfactant.

The amine oxides used in forming the analephotropic complex are depicted by the formula

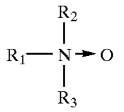

wherein $R_1$ is a $C_{10}$–$C_{18}$ a linear or branched chain alkyl group, $R_2$ is a $C_1$–$C_{16}$ linear alkyl group and $R_3$ is a $C_1$–$C_{16}$ linear alkyl group.

The zwitterionic surfactant used in forming the analephotropic complex is a water soluble betaine having the general formula:

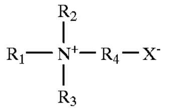

wherein $X^-$ is selected from the group consisting of $COO^-$ and $SO_3^-$ and $R_1$ is an alkyl group having 10 to about 20 carbon atoms, preferably 12 to 16 carbon atoms, or the amido radical:

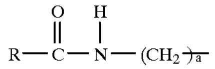

wherein R is an alkyl group having about 9 to 19 carbon atoms and a is the integer 1 to 4: $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine. Three preferred betaine surfactants are Genagen CAB and Rewoteric AMB 13 and Golmschmidt Betaine L7.

The alkylene carbonate surfactant is depicted by the following formula:

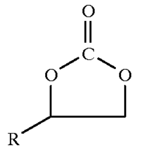

wherein R is an alkyl group having about 4 to about 14 carbon atoms, more preferably about 6 to about 10 carbon atoms.

The instant compositions contain about 0.1 to 2.0 wt. %, more preferably 0.1 to 1.0 wt. % of a protein chemical linker which is selected from the group consisting of vegetable proteins and animal proteins and mixtures thereof.

Typical vegetable proteins used in the instant composition derived from wheat. Typical vegetable proteins are hydrolyzed wheat protein such as Gluadin APG ex Henkel.

Other proteins that can be used in the instant compositions are naturein protein hydrolysates of vegetable origin including, Casein Peptide AS (hydrolysate casein) from Quest international of low molecular weight distribution, typically, <1 kDalton (88%), 5–1 kDalton (10%), >5 kDalton (2%), or Casein Peptide HY (hydrolysate casein) from Quest international of higher molecular weight distribution, typically, <1 kDalton (40%), 5–1 kDalton (20%), >5 kDalton (40%), or Gluadin W 20 (hydrolysed wheat gluten) from Henkel, of approximative molecular weight 4.5 kDalton, and Gluadin Almond (hydrolysed almond protein) from Henkel, of approximative molecular weight 4 kDalton, and mixtures thereof.

Typical animal proteins used in the instant compositions are Norlan LVC hydrolysed animal collagen from Proalan Company (Barcelona - Spain), Nutrilan FPK hydrolysed animal collagen from Henkel, Elastinhydrolysate hydrolysed animal elastine from Henkel.

A cosurfactant can be optionally used in forming the cleaning compositions of the instant invention. Suitable cosurfactants over temperature ranges extending from 4° C. to 43° C. are: (1) water-soluble $C_3$–$C_4$ alkanols, polypropylene glycol of the formula $HO(CH_3CHCH_2O)_nH$ wherein n is a number from 2 to 18 and copolymers of ethylene oxide and propylene oxide and mono $C_1$–$C_6$ alkyl ethers and esters of ethylene glycol and propylene glycol having the structural formulas $R(X)_nOH$ and $R_1(X)_nOH$ wherein R is $C_1$–$C_6$ alkyl, $R_1$ is $C_2$–$C_4$ acyl group, X is $(OCH_2CH_2)$ or $(OCH_2(CH_3)CH)$ and n is a number from 1 to 4.

Representative members of the polypropylene glycol include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), triethylene glycol monobutyl ether, mono, di, tri propylene glycol monobutyl ether, tetraethylene glycol monobutyl ether, mono, di, tripropylene glycol monomethyl ether, propylene glycol monomethyl ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono, di, tripropylene glycol monoethyl ether, mono, di tripropylene glycol monopropyl ether, mono, di, tripropylene glycol monopentyl ether, mono, di, tripropylene glycol monohexyl ether, mono, di, tributylene glycol mono methyl ether, mono, di, tributylene glycol monoethyl ether, mono, di, tributylene glycol monopropyl ether, mono, di, tributylene glycol monobutyl ether, mono, di, tributylene glycol monopentyl ether and mono, di, tributylene glycol monohexyl ether, ethylene glycol monoacetate and dipropylene glycol propionate. Representative members of the aliphatic carboxylic acids include $C_3$–$C_6$ alkyl and alkenyl monobasic acids such as acrylic acid and propionic acid and dibasic acids such as glutaric acid and mixtures of glutaric acid with adipic acid and succinic acid, as well as mixtures of the foregoing acids.

While all of the aforementioned glycol ether compounds and acid compounds provide the described stability, the most preferred cosurfactant compounds of each type, on the basis of cost and cosmetic appearance (particularly odor), are diethylene glycol monobutyl ether and a mixture of adipic, glutaric and succinic acids, respectively. The ratio of acids in the foregoing mixture is not particularly critical and can be modified to provide the desired odor. Generally, to maximize water solubility of the acid mixture glutaric acid, the most water-soluble of these three saturated aliphatic dibasic acids, will be used as the major component.

Still other classes of cosurfactant compounds providing stable cleaning compositions at low and elevated temperatures are the mono-, di- and triethyl esters of phosphoric acid such as triethyl phosphate.

The amount of cosurfactant which might be required to stabilize the cleaning compositions will, of course, depend on such factors as the surface tension characteristics of the cosurfactant, the type and amounts of the analephotropic complex and perfumes, and the type and amounts of any other additional ingredients which may be present in the composition and which have an influence on the thermodynamic factors enumerated above. Generally, amounts of cosurfactant in the range of from 0 to 50 wt. %, preferably from 0.1 wt. % to 25 wt. %, especially preferably from 0.5 wt. % to 15 wt. %, by weight provide stable microemulsions for the above-described levels of primary surfactants and perfume and any other additional ingredients as described below.

The water insoluble saturated or unsaturated organic compounds contain 4 to 20 carbon atoms and up to 4 different or identical functional groups and is used at a concentration of about 1.0 wt. % to about 8 wt. %, more preferably about 2.0 wt. % to about 7 wt. %. Examples of acceptable water insoluble saturated or unsaturated organic compound include (but are not limited to) water insoluble hydrocarbons containing 0 to 4 different or identical functional groups, water insoluble aromatic hydrocarbons containing 0 to 4 different or identical functional groups, water insoluble heterocyclic compounds containing 0 to 4 different or identical functional groups, water insoluble ethers containing 0 to 3 different or identical functional groups, water insoluble alcohols containing 0 to 3 different or identical functional groups, water insoluble amines containing 0 to 3 different or identical functional groups, water insoluble esters containing 0 to 3 different or identical functional groups, water insoluble carboxylic acids containing 0 to 3 different or identical functional groups, water insoluble amides containing 0 to 3 different or identical functional groups, water insoluble nitrites containing 0 to 3 different or identical functional group, water insoluble aldehydes containing 0 to 3 different or identical functional groups, water insoluble ketones containing 0 to 3 different or identical functional groups, water insoluble phenols containing 0 to 3 different or identical functional groups, water insoluble nitro compounds containing 0 to 3 different or identical functional groups, water insoluble halogens containing 0 to 3 different or identical functional groups, water insoluble sulfates or sulfonates containing 0 to 3 different or identical functional groups, limonene, dipentene, terpineol, essential oils, perfumes, water insoluble organic compounds containing up to 4 different or identical functional groups such as an alkyl cyclohexane having both three hydroxys and one ester group and mixture thereof.

Typical heterocyclic compounds are 2,5-dimethylhydrofuran,2-methyl-1,3-dioxolane, 2-ethyl 2-methyl 1,3 dioxolane, 3-ethyl 4-propyl tetrahydropyran, 3-morpholino-1,2-propanediol and N-isopropyl morpholine A typical amine is alpha-methyl benzyldimethylamine. Typical halogens are 4-bromotoluene, butyl chloroform and methyl perchloropropane. Typical hydrocarbons are 1,3-dimethylcyclohexanone, cyclohexyl-1 decane, methyl-3 cyclohexyl-9 nonane, methyl-3 cyclohexyl-6 nonane, dimethyl cycloheptane, trimethyl cyclopentane, ethyl-2 isopropyl-4 cyclohexane. Typical aromatic hydrocarbons are bromotoluene, diethyl benzene, cyclohexyl bromoxylene, ethyl-3 pentyl-4 toluene, tetrahydronaphthalene, nitrobenzene and methyl naphthalene. Typical water insoluble esters are benzyl acetate, dicyclopentadienylacetate, isononyl acetate, isobornyl acetate and isobutyl isobutyrate. Typical water insoluble ethers are di(alphamethyl benzyl) ether and diphenyl ether. Typical alcohols are phenoxyethanol and 3-morpholino-1,2-propanediol. Typical water insoluble nitro derivatives are nitro butane and nitrobenzene.

Suitable essential oils are selected from the group consisting of: Anethole 20/21 natural, Aniseed oil china star, Aniseed oil globe brand, Balsam (Peru), Basil oil (India), Black pepper oil, Black pepper oleoresin 40/20, Bois de Rose (Brazil) FOB, Borneol Flakes (China), Camphor oil, White, Camphor powder synthetic technical, Cananga oil (Java), Cardamom oil, Cassia oil (China). Cedarwood oil (China) BP, Cinnamon bark oil, Cinnamon leaf oil, Citronella oil, Clove bud oil, Clove leaf, Coriander (Russia), Coumarin 69° C. (China), Cyclamen Aldehyde, Diphenyl oxide, Ethyl vanilin, Eucalyptol, Eucalyptus oil, Eucalyptus citriodora, Fennel oil, Geranium oil, Ginger oil, Ginger oleoresin (India), White grapefruit oil, Guaiacwood oil, Gurjun balsam, Heliotropin, Isobornyl acetate, Isolongifolene, Juniper berry oil, L-methyl acetate, Lavender oil, Lemon oil, Lemongrass oil, Lime oil distilled, Litsea Cubeba oil, Longifolene, Menthol crystals, Methyl cedryl ketone, Methyl chavicol, Methyl salicylate, Musk ambrette, Musk ketone, Musk xylol, Nutmeg oil, Orange oil, Patchouli oil, Peppermint oil, Phenyl ethyl alcohol, Pimento berry oil, Pimento leaf oil, Rosalin, Sandalwood oil, Sandenol, Sage oil, Clary sage, Sassafras oil, Spearmint oil, Spike lavender, Tagetes, Tea tree oil, Vanilin, Vetyver oil (Java), Wintergreen, Allocimene, Arbanex™, Arbanol®, Bergamot oils, Camphene, Alpha-Campholenic aldehyde, I-Carvone, Cineoles, Citral, Citronellol Terpenes, Alpha-Citronellol, Citronellyl Acetate, Citronellyl Nitrile, Para-Cymene, Dihydroanethole, Dihydrocarveol, d-Dihydrocarvone, Dihydrolinalool, Dihydromyrcene, Dihydromyrcenol, Dihydromyrcenyl Acetate, Dihydroterpineol, Dimethyloctanal, Dimethyloctanol, Dimethyloctanyl Acetate, Estragole, Ethyl-2 Methylbutyrate, Fenchol, Fernol™, Florilys™, Geraniol, Geranyl Acetate, Geranyl Nitrile, Glidmint™ Mint oils, GlidoX™, Grapefruit oils, trans-2-Hexenal, trans-2-Hexenol, cis-3-Hexenyl Isovalerate, cis-3-Hexanyl-2-methylbutyrate, Hexyl Isovalerate, Hexyl-2-methylbutyrate, Hydroxycitronellal, lonone, Isobornyl Methylether, Linalool, Linalool Oxide, Linalyl Acetate, Menthane Hydroperoxide, 1-Methyl Acetate, Methyl Hexyl Ether, Methyl-2-methylbutyrate, 2-Methylbutyl Isovalerate, Myrcene, Nerol, Neryl Acetate, 3-Octanol, 3-Octyl Acetate, Phenyl Ethyl-2-methylbutyrate, Petitgrain oil, cis-Pinane, Pinane Hydroperoxide, Pinanol, Pine Ester, Pine Needle oils, Pine oil, alpha-Pinene, beta-Pinene, alpha-Pinene Oxide, Plinol, Plinyl Acetate, Pseudo lonone, Rhodinol, Rhodinyl Acetate, Spice oils, alpha-Terpinene, gamma-Terpinene, Terpinene-4-OL, Terpineol, Terpinolene, Terpinyl Acetate, Tetrahydrolinalool, Tetrahydrolinalyl Acetate, Tetrahydromyrcenol, Tetralol®, Tomato oils, Vitalizair, Zestoral™.

In addition to the above-described essential ingredients required for the formation of the cleaning compositions, the compositions of this invention may often and preferably do contain one or more additional ingredients which serve to improve overall product performance.

One such ingredient is an inorganic or organic salt of oxide of a multivalent metal cation, particularly $Mg^{++}$. The metal salt or oxide provides several benefits including improved cleaning performance in dilute usage, particularly in soft water areas, and minimized amounts of perfume required to obtain the microemulsion state. Magnesium sulfate, either anhydrous or hydrated (e.g., heptahydrate), is especially preferred as the magnesium salt. Good results also have been obtained with magnesium oxide, magnesium chloride, magnesium acetate, magnesium propionate and magnesium hydroxide. These magnesium salts can be used with formulations at neutral or acidic pH since magnesium hydroxide will not precipitate at these pH levels.

Although magnesium is the preferred multivalent metal from which the salts (inclusive of the oxide and hydroxide) are formed, other polyvalent metal ions also can be used provided that their salts are nontoxic and are soluble in the aqueous phase of the system at the desired pH level.

Thus, depending on such factors as the pH of the system, the nature of the analephotropic complex or anionic surfactant and cosurfactant, as well as the availability and cost factors, other suitable polyvalent metal ions include aluminum, copper, nickel, iron, calcium, etc. It should be noted, for example, that with the preferred paraffin sulfonate anionic detergent calcium salts will precipitate and should not be used. It has also been found that the aluminum salts work best at pH below 5 or when a low level, for example 1 weight percent, of citric acid is added to the composition which is designed to have a neutral pH. Alternatively, the aluminum salt can be directly added as the citrate in such case. As the salt, the same general classes of anions as mentioned for the magnesium salts can be used, such as halide (e.g., bromide, chloride), sulfate, nitrate, hydroxide, oxide, acetate, propionate, etc.

The cleaning compositions can optionally include from 0 to 2.5 wt. %, preferably from 0.1 wt. % to 2.0 wt. % of the composition of a $C_8$–$C_{22}$ fatty acid or fatty acid soap as a foam suppressant. The addition of fatty acid or fatty acid soap provides an improvement in the rinseability of the composition whether applied in neat or diluted form. Generally, however, it is necessary to increase the level of cosurfactant to maintain product stability when the fatty acid or soap is present. If more than 2.5 wt. % of a fatty acid is used in the instant compositions, the composition will become unstable at low temperatures as well as having an objectionable smell.

As example of the fatty acids which can be used as such or in the form of soap, mention can be made of distilled coconut oil fatty acids, "mixed vegetable" type fatty acids (e.g. high percent of saturated, mono-and/or polyunsaturated $C_{18}$ chains); oleic acid, stearic acid, palmitic acid, eiocosanoic acid, and the like, generally those fatty acids having from 8 to 22 carbon atoms being acceptable.

The liquid cleaning compositions of this invention may, if desired, also contain other components either to provide additional effect or to make the product more attractive to the consumer. The following are mentioned by way of example: Colors or dyes in amounts up to 0.5% by weight; bactericides in amounts up to 1 % by weight; preservatives or antioxidizing agents, such as formalin, 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

In final form, the cleaning compositions exhibit stability at reduced and increased temperatures. More specifically, such compositions remain clear and stable in the range of 4° C. to 50° C., especially 10° C. to 43° C. Such compositions exhibit a pH in the acid or neutral range depending on intended end use. The liquids are readily pourable and exhibit a viscosity in the range of 6 to 60 milliPascal-Second (mPas.) as measured at 25° C. with a Brookfield RVT Viscometer using a #1 spindle rotating at 20 RPM. Preferably, the viscosity is maintained in the range of 10 to 40 mpas.

The compositions are directly ready for use or can be diluted as desired and in either case no or only minimal rinsing is required and substantially no residue or streaks are left behind. When intended for use in the neat form, the liquid compositions can be packaged under pressure in an aerosol container or in a pump-type sprayer for the so-called spray-and-wipe type of application.

Because the compositions as prepared are aqueous liquid formulations and since no particular mixing is required to form the all purpose cleaning or microemulsion composition, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents and cosurfactants can be separately prepared and combined with each other and with the perfume. The magnesium salt, or other multivalent metal compound, when present, can be added as an aqueous solution thereof or can be added directly. It is not necessary to use elevated temperatures in the formation step and room temperature is sufficient.

The following examples illustrate the liquid cleaning compositions containing protein chemical linkers. Unless otherwise specified, all percentages are by weight. The exemplified compositions are illustrative only and do not limit the scope of the invention. Unless otherwise specified, the proportions in the examples and elsewhere in the specification are by weight.

EXAMPLE 1

The following cleaning compositions in wt. % with protein chemical linker were made by simple mixing at 25° C. and tested for cleaning performance.

| Raw Materials | A | B | C | D | E |
|---|---|---|---|---|---|
| Magnesium $C_9$–$C_{13}$ linear alkylbenzene sulfonate (LAS) (50%) | 2.34 | 2.34 | 2.34 | 2.34 | 2.34 |
| Sodium $C_9$–$C_{13}$ linear alkylbenzene sulfonate (LAS) (50%) | 2.34 | 2.34 | 2.34 | 2.34 | 2.34 |
| Cocoamidopropyl betaine (CAPB) (30%) | 0.82 | 0.82 | 0.82 | 0.82 | 0.82 |
| Dipropylene glycol mono methyl ether (DPM) | 5.1 | 4.0 | 4.0 | — | — |
| Diethylene glycol mono n-butyl ether (DEGMBE) | — | — | — | 4.1 | 4.6 |
| Collagen hydrolysate (Norlan LVC 55%) | — | 1.0 | 0.5 | 0.5 | — |
| Hydrolyzed wheat gluten (Gluadin AGP 90%) | — | — | — | — | 0.5 |
| Perfume | 0.63 | 0.63 | 0.63 | 0.63 | 0.63 |
| Water | Bal. | Bal. | Bal. | Bal. | Bal. |

Samples A–E also contain required amount of sodium hydroxyde to ajust the pH to 6.9–7.0.

Cleaning performance were performed at 25° C. on Samples A–E

| Tests | A | B | C | D | E |
|---|---|---|---|---|---|
| % Particulate soil removal "Kaolin" soil[a] | 47 | 87 | 81 | 74 | 84 |

(a) "Kaolin" particulate soil composition: 70 g mineral oil, 35 g kaolin and 35 g tetrachloroethylene as solvent carrier (tetrachloroethylene is removed in an oven at 80° C. prior to run the test). Kaolin is medium particle size china clay from ECC International—grade E powder—65% minimum below 10 microns, with 0.05% maximum above 53 microns.

What is claimed is:

1. A cleaning composition consisting of approximately by weight:

(a) 0.1% to 2% of a protein chemical linker, which is selected from the group consisting of hydrolyzed wheat and collagen hydrolyzate;

(b) 0.5% to 30% of at least one anionic surfactant having a carboxylate, sulfate or sulfonate group;

(c) 3% to 15% of a second surfactant is an alkylene carbonate surfactants; and (d) 50% to 99.8% of water.

* * * * *